United States Patent
Jensen et al.

(10) Patent No.: US 10,071,149 B2
(45) Date of Patent: Sep. 11, 2018

(54) **TEMPERATURE SENSITIVE MULTIVALENT *BORDETELLA AVIUM* VACCINES**

(71) Applicant: BRIGHAM YOUNG UNIVERSITY, Provo, UT (US)

(72) Inventors: Marcus M. Jensen, Provo, UT (US); Richard A. Robison, Provo, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 7 days.

(21) Appl. No.: 15/586,110

(22) Filed: May 3, 2017

(65) Prior Publication Data

US 2017/0319677 A1 Nov. 9, 2017

Related U.S. Application Data

(60) Provisional application No. 62/331,266, filed on May 3, 2016.

(51) Int. Cl.
| | | |
|---|---|---|
| *A61K 39/10* | (2006.01) | |
| *A61K 49/00* | (2006.01) | |
| *A61K 39/02* | (2006.01) | |
| *C12P 1/04* | (2006.01) | |
| *A61K 39/00* | (2006.01) | |

(52) U.S. Cl.
CPC ............... *A61K 39/099* (2013.01); *C12P 1/04* (2013.01); *A61K 2039/522* (2013.01); *A61K 2039/552* (2013.01); *A61K 2039/70* (2013.01)

(58) Field of Classification Search
CPC .................................. A61K 39/00; A61K 39/02
USPC .............................. 424/93.1, 93.2, 93.3, 93.4
See application file for complete search history.

(56) References Cited

U.S. PATENT DOCUMENTS

| | | |
|---|---|---|
| 4,379,140 A | 4/1983 | Jensen |
| 4,867,975 A | 9/1989 | Gelb, Jr. |
| 6,077,516 A | 6/2000 | Nagaraja et al. |

FOREIGN PATENT DOCUMENTS

| | | |
|---|---|---|
| CN | 102458462 A | 5/2012 |
| WO | 2008118592 A2 | 10/2008 |
| WO | 2010094064 A1 | 8/2010 |

OTHER PUBLICATIONS

Devi P. Patnayak et al., Experimental and Field Evaluation of a Live Vaccine Against Avian Pneumovirus, Avian Pathology (2002) vol. 31, pp. 377-382.
Mark W. Jackwood, PhD, Overview of Bordetellosis in Poultry, Merck Vetrinary Manual, 2016, http://www.merckvetmanual.com/poultry/bordetellosis/overview-of-bordetellosis-in-poultry, pp. 1-7.
D.S.Burke et al., Immunization Against Turkey Coryza by Colonization with Mutants of Alcaligenes Faecalis, Avian Diseases, vol. 24, No. 3, Mar. 17, 1980, pp. 726-733.
D.S. Burke et al., Field Vaccination Trials Against Turkey Coryza Using a Temperature-Sensitive Mutant of Alcaligenes Faecalis, Avian Diseases, vol. 25, No. 1, Jun. 13, 1980, pp. 96-103.
M.M. Jensen et al., Control of Turkey Alcaligenes Rhinotracheitis in Utah With a Live Vaccine, Avian Diseases, vol. 25, No. 4, May 19, 1981, pp. 1053-1057.

*Primary Examiner* — Rodney P Swartz
(74) *Attorney, Agent, or Firm* — Brooks Kushman P.C.

(57) ABSTRACT

The present invention is related to various vaccine compositions against *Bordetella avium* and methods for preparing and administering the various vaccine compositions. The present invention is related to multivalent vaccines compositions such as bivalent or trivalent vaccines for inoculating turkeys against from *Bordetella avium* rhinotracheitis or coryza due to *Bordetella avium* infection as well as methods of preparing and administering the multivalent vaccine compositions.

17 Claims, 2 Drawing Sheets

FIG. 1

Growth Curve for *B. avium* mutants at 32° C

- – · – BB-1 32° C
- – · · – CS-9 32° C
- · · · · · OC-2 32° C
- · · · · · BB-1 40° C
- ——— CS-9 40° C
- – – – OC-2 40° C

TEMPERATURE SENSITIVE MULTIVALENT *BORDETELLA AVIUM* VACCINES

CROSS-REFERENCE TO RELATED APPLICATIONS

This application claims the benefit of U.S. provisional application Ser. No. 62/331,266 filed 3 May 2016, the disclosure of which is hereby incorporated in its entirety by reference herein.

TECHNICAL FIELD

In at least one aspect, the present invention is related to various vaccine compositions against *Bordetella avium* and methods for preparing and administering the various vaccine compositions.

BACKGROUND

Avian bordetellosis has been identified in almost every area of the world where turkeys are intensively reared. Studies suggest that among domesticated turkeys in the Eastern U.S., about 50% are exposed to the bacterium throughout their lifetime. This disease is a highly infectious, acute upper respiratory tract infection of turkeys characterized by high morbidity and usually low mortality. The disease is usually of sudden onset within the flock and morbidity may reach 100% within 24 hours. Mortality varies, but is usually understood to be a disease of high morbidity and low mortality, however, mortality rates will rise if concurrent infections are present in the flock and if ventilation and environmental conditions are poor.

Historical vaccination with bacterins and a live temperature-sensitive mutant vaccine have given mixed results depending on the age of the turkey and the method of administration. Typically, less than 3 weeks old turkeys (e.g. poults) respond positively to vaccination with the live temperature-sensitive vaccine. Currently, vaccination is not widely practiced by turkey breeders, and the immunity that is passed to progeny generally comes from natural infections.

*Bordetella avium* is easily carried between farms. Normally, prevention includes a good biosecurity program with rigorous cleanup and disinfection after field outbreaks. Most of the commonly used disinfectants are somewhat effective.

The vaccine, known as the ART VAX®, is a live attenuated vaccination against *Bordetella avium* (also previously known as *Alcaligenes faecalis*), which is the etiological agent of turkey coryza causing significant problems for the turkey industry. The ART VAX® vaccine has been available commercially since its creation and has saved the turkey industry millions of dollars in losses. The vaccine was created by selection of temperature sensitive mutants from the wild type. These mutants were able to survive in the cooler nasal mucosa of young poults, but unable to replicate in the warmer lower respiratory tract. In recent years, the ART VAX® vaccine seems to have decreased efficacy, possibly because of the emergence of new strains of *Bordetella avium* in turkey populations.

Accordingly there is a need for an improved vaccine against *Bordetella avium* strains.

SUMMARY

In at least one aspect, the present invention is related to various vaccine compositions against *Bordetella avium* and methods for preparing and administering the various vaccine compositions.

In various embodiments are disclosed various vaccine compositions against *Bordetella avium* and methods for preparing and administering the various vaccine compositions.

In various embodiments are disclosed a temperature sensitive *Bordetella avium* multivalent vaccine comprising: a pharmaceutically acceptable carrier; and a plurality of different temperature sensitive *Bordetella avium* strains that are stably unable to colonize lower tracheas and lungs of turkey poults.

In various embodiments are disclosed a method of preparing a temperature sensitive *Bordetella avium* multivalent vaccine, the method comprising the steps of: isolating a plurality of *Bordetella avium* isolates from turkey poults, where each of the *Bordetella avium* isolates are acquired at different geographic locations; individually exposing each of the plurality of *Bordetella avium* isolates to a mutagenic agent; individually culturing each of the plurality of *Bordetella avium* isolates after exposure with the mutagenic agent; isolating a temperature sensitive *Bordetella avium* strain from each culture of the plurality of *Bordetella avium* isolates, wherein each of the temperature sensitive *Bordetella avium* strains at 32° C. stably grows at a rate and at 40° C. grows at a rate slower than the rate at 32° C.; and combining immunologically effective amounts of each of the temperature sensitive *Bordetella avium* strains with a pharmaceutically acceptable carrier.

In various embodiments are disclosed a method of immunizing turkey poults against *Bordetella avium*, comprising a step of administering to a turkey poult an immunologically effective amount of a temperature sensitive *Bordetella avium* multivalent vaccine comprising a pharmaceutically acceptable carrier and a plurality of different temperature sensitive *Bordetella avium* strains that are stably unable to colonize lower tracheas and lungs of the turkey poults.

In various embodiments are disclosed a temperature sensitive *Bordetella avium* multivalent vaccine prepared by a process comprising the steps of: isolating a plurality of *Bordetella avium* isolates from turkey poults, where each of the *Bordetella avium* isolates is acquired at a different geographic location; separately exposing each of the plurality of *Bordetella avium* isolates to a mutagenic agent; separately culturing each of the plurality of *Bordetella avium* isolates after exposure with the mutagenic agent; isolating a temperature sensitive *Bordetella avium* strain from each culture of the plurality of *Bordetella avium* isolates, wherein each of the temperature sensitive strains at 32° C. stably grows at a rate and at 40° C. grows at a rate slower than the rate at 32° C.; and combining immunologically effective amounts of each of the temperature sensitive *Bordetella avium* strains with a pharmaceutically acceptable carrier.

U.S. Pat. No. 4,379,140, which issued on Apr. 5, 1983, is incorporated herein by reference.

BRIEF DESCRIPTION OF THE DRAWINGS

FIG. 1 is a graphical representation showing growth curves for temperature sensitive *Bordetella avium* strains of various embodiments of the present invention over a time period.

DETAILED DESCRIPTION

Figure 2:
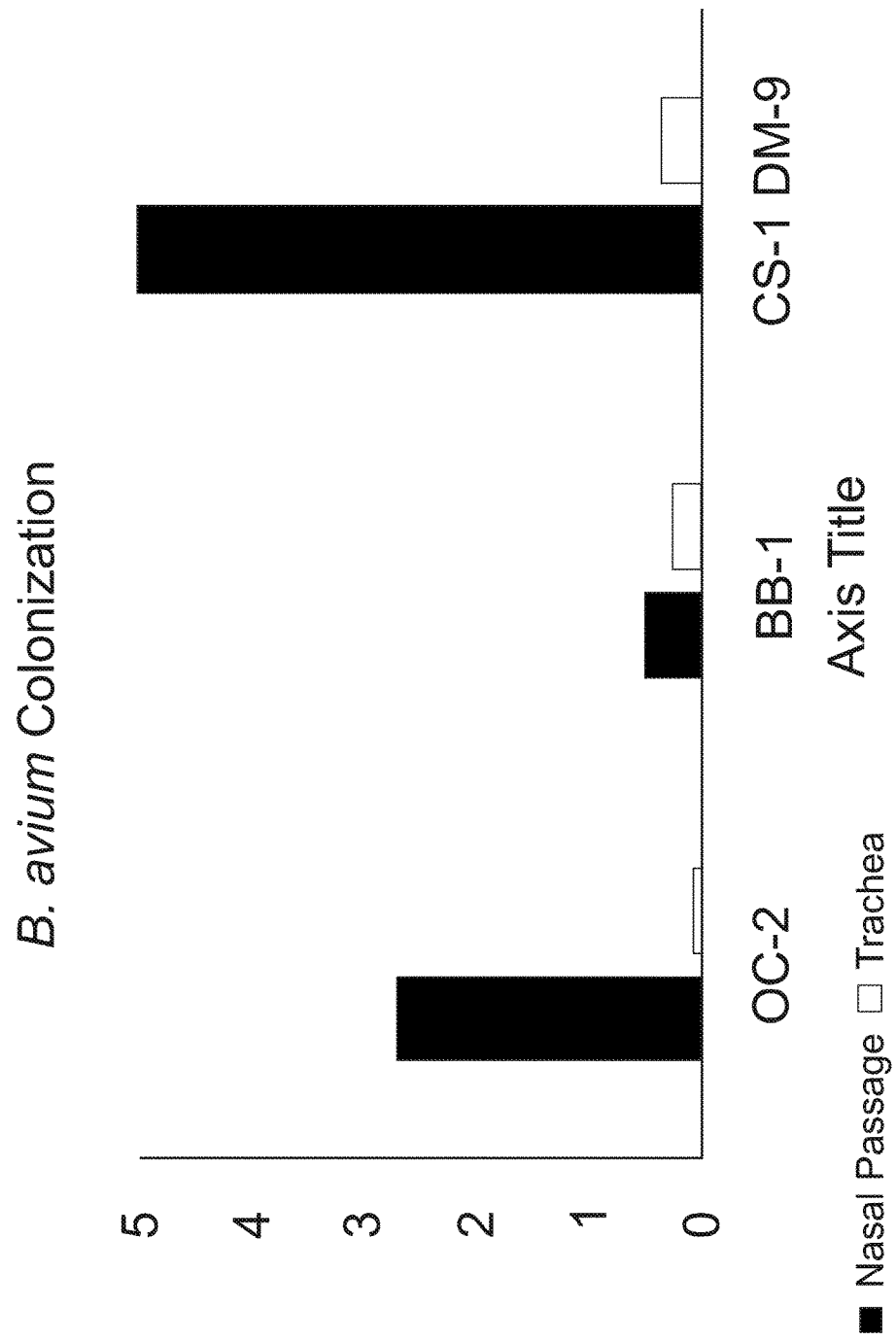
FIG. 2 is a graphical representation show levels of colonization of temperature sensitive *Bordetella avium* strains of various embodiments of the present invention in nasal passageways and tracheas.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. The first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

Throughout this application, where publications are referenced, the disclosures of these publications in their entireties are hereby incorporated by reference into this application to more fully describe the state of the art to which this invention pertains.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

In at least one aspect, the present invention is related to various vaccine compositions against *Bordetella avium* and methods for preparing and administering the various vaccine compositions. In various embodiments are disclosed various vaccine compositions against *Bordetella avium* and methods for preparing and administering the various vaccine compositions.

In various embodiments are disclosed temperature sensitive *Bordetella avium* multivalent vaccines comprising: a pharmaceutically acceptable carrier; and a plurality of different temperature sensitive *Bordetella avium* strains that are stably unable to colonize lower tracheas and lungs of the turkey poults. The pharmaceutically acceptable carrier of various embodiments can include any carrier that preferably does not itself induce the production of antibodies harmful to the individual receiving the composition such as, for example, water, proteins, polysaccharides, polylactic acids, polyglycolic acids, polymeric amino acids, amino acid copolymers, lipid aggregates (such as oil droplets or liposomes).

In other embodiments, the temperature sensitive *Bordetella avium* multivalent vaccine is able to inoculate other domesticated avian species such as, for example, chickens, geese, ducks, and fowls.

In various embodiments, the multivalent vaccine comprises 50 to 200 million bacteria that preferably includes the plurality of different temperature sensitive *Bordetella avium* strains. The multivalent vaccine comprises 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, and 200 bacteria. In various embodiments, the multivalent vaccine comprises between any two amounts of bacteria from above.

In various embodiments, any strain of the plurality of different temperature sensitive *Bordetella avium* strains can be 0.5%, 1%, 10%, 15%, 20%, 25%, 30%, 35%, 40%, 45%, 50%, 55%, 60%, 65%, 70%, 75%, 80%, 85%, 90%, 95%, and 99% of the total bacterial concentration of the vaccine. In various embodiments, any strain of the plurality of different temperature sensitive *Bordetella avium* strains can be between any two percentages from above of the total bacterial concentration of the vaccine. In various embodiments, the total bacterial concentration of the vaccine is made up of the plurality of different temperature sensitive *Bordetella avium* strains.

In various embodiments, at least one or each of the plurality of different temperature sensitive *Bordetella avium* strains has a different colonization rate in the nasal and upper trachea mucosa after administration. The colonization rate of the different temperature sensitive *Bordetella avium* strains of various embodiments can vary by 5%, 10%, 15%, 20%, 25%, 30%, 35%, 40%, 45%, 50%, 55%, 60%, 65%, 70%, 75%, 80%, 85%, 90%, 95%, and 100%. In various embodiments, the colonization rate can vary between any two percentages from above.

In various embodiments, the plurality of temperature sensitive *Bordetella avium* strains are two temperature sensitive *Bordetella avium* strains such that the multivalent vaccine is a bivalent vaccine. In various embodiments, the plurality of temperature sensitive strains of *Bordetella avium* are three temperature sensitive *Bordetella avium* strains such that the multivalent vaccine is a trivalent vaccine. Also in other embodiments, the plurality of temperature sensitive *Bordetella avium* strains are four temperature sensitive *Bordetella avium* strains such that the multivalent vaccine is a quadrivalent vaccine.

In various embodiments, at least one or each of the plurality of temperature sensitive *Bordetella avium* strains stably grows at a rate at 32° C. and at 40° C. grows at a rate slower than the rate at 32° C. In various embodiments, at least one or each of the plurality of temperature sensitive *Bordetella avium* strains grows at a rate 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, and 50% of the rate at 32° C. In various embodiments, at least one or each of the plurality of temperature sensitive *Bordetella avium* strains stably grows at a rate between any two percentages from above of the rate at 32° C.

In various embodiments, at least one or each of the plurality of temperature sensitive strains of *Bordetella avium* stably grows at 32° C. and not at 40° C.

In various embodiments, the stability of at least one or each of the plurality of temperature sensitive *Bordetella avium* strains is such that the strains have been back passed 5, 6, 7, 8, 9, and 10 times in the nasal mucosa of turkeys and shows no signs of changes in growth characteristics or virulence and is thus considered to be genetically stable. In various embodiments, the stability of at least one or each of the plurality of temperature sensitive *Bordetella avium* strains are shown through back passage between any two times from above in the nasal mucosa of turkeys.

In various embodiments, at least one of the of the plurality of temperature sensitive *Bordetella avium* strains is genomically similar to strain 87, which has been previously deposited as ATCC No. 31770 as indicated in U.S. Pat. No. 4,379,140. In various embodiments, at least one of the of the plurality of temperature sensitive *Bordetella avium* strains is not genomically similar to strain 87 or vaccine strain 87 of *Bordetella avium*, which has been previously deposited as American Type Culture Collection of Rockville, Md. (ATCC) and assigned ATCC No. 31770 as indicated in U.S. Pat. No. 4,379,140.

In various embodiments, at least one of the of the plurality of temperature sensitive *Bordetella avium* strains has a matrix-assisted laser desorption/ionization time of flight spectra that does not cluster with vaccine strain 87.

In various embodiments, at least one or each of the plurality of temperature sensitive *Bordetella avium* strains stably grows at a rate of about 30° C., 31° C., 32° C., 33° C., and 34° C. In various embodiments, at least one or each of the plurality of temperature sensitive *Bordetella avium* strains stably grows at a rate between any two rates from above.

In various embodiments, at least one or each of the plurality of temperature sensitive *Bordetella avium* strains grows about or at least 40° C., 41° C., and 42° C. at a rate slower than the rate of about 30° C., 31° C., 32° C., 33° C., and 34° C. In various embodiments, at least one or each of the plurality of temperature sensitive *Bordetella avium* strains grows at a rate between any two rates from above. Alternatively, at least one or each of the plurality of temperature sensitive *Bordetella avium* strains does not grow at a temperature of about or at least 40° C., 41° C., and 42° C. In various embodiments, at least one or each of the plurality of temperature sensitive *Bordetella avium* strains does not grow at between any two of about temperatures from about or at least temperatures from above.

In various embodiments, the plurality of temperature sensitive *Bordetella avium* strains are derived from *Bordetella avium* isolates isolated from turkey poults that died from *Bordetella avium* rhinotracheitis. The *Bordetella avium* isolates of various embodiments belong to *Bordetella avium* strains having a mortality rate that is greater than 15% in turkeys. Also, the *Bordetella avium* isolates of various embodiments are isolated at different geographic locations such as, for example, turkey farms.

In various embodiments, *Bordetella avium* isolates belong to *Bordetella avium* strains that results in *Bordetella avium* rhinotracheitis and/or turkey coryza in turkeys. In various embodiments, the mortality rate of infections of the *Bordetella avium* strains is about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% in turkeys. In various embodiments, the mortality rate of infections of the *Bordetella avium* strains is between any two percentages from above.

In various embodiments are disclosed methods of preparing a temperature sensitive *Bordetella avium* multivalent vaccine, the method comprising the steps of: isolating a plurality of *Bordetella avium* isolates from turkey poults, where each of the *Bordetella avium* isolates are acquired at different geographic locations (i.e. turkey farms); individually exposing each of the plurality of *Bordetella avium* isolates to a mutagenic agent; individually culturing each of the plurality of *Bordetella avium* isolates after exposure with the mutagenic agent; isolating a temperature sensitive *Bordetella avium* strain from each culture of the plurality of *Bordetella avium* isolates, wherein each of the temperature sensitive *Bordetella avium* strains at 32° C. stably grows at a rate and at 40° C. grows at a rate slower than the rate at 32° C.; and combining immunologically effective amounts of each of the temperature sensitive *Bordetella avium* strains with a pharmaceutically acceptable carrier. The temperature sensitive *Bordetella avium* strains are preferably not virulent that can mean in various embodiments slower growth rates, reduced severity of the diseases/symptoms, or both. More preferably, temperature sensitive *Bordetella avium* strains of various embodiments only provide minor symptoms to the poults.

In various embodiments, the *Bordetella avium* isolates are derived from different *Bordetella avium* strains that cluster or do not cluster with vaccine strain 87 according to spectras acquired from matrix-assisted laser desorption/ionization time of flight mass (MALDI-TOF) spectroscopy and analyzed via cluster analysis. In other embodiments, at least one *Bordetella avium* strain clusters with vaccine strain 87 and at least one *Bordetella avium* strain does not cluster with vaccine strain 87.

In various embodiments, MALDI-TOF spectras are acquired from the plurality of *Bordetella avium* isolates and compared with the MALDI-TOF spectra of the vaccine strain 87 by cluster analysis. In one embodiment, the vaccine includes a temperature sensitive *Bordetella avium* strain prepared from an isolate of a *Bordetella avium* strain that does not cluster with vaccine strain 87.

In various embodiments, examples of mutagenic agents includes various alkylating agents such as N-methyl-N'-nitro-N-nitrosoguanidine (NTG). In various embodiments, the *Bordetella avium* isolates are exposed to a concentration of about 300 µg, 350 µg, 400 µg, 450 µg, 500 µg, 550 µg, 600 µg, 650 µg, 700 µg, 750 µg, 800 µg, 850 µg, 900 µg, 950 µg, and 1000 µg of the mutagenic agent. In various embodiments, the *Bordetella avium* isolates are exposed to a concentration between any two concentrations of mutagenic agent from above.

In various embodiments, the *Bordetella avium* isolates are exposed to the mutagenic agent for about 30 minutes, 35 minutes, 40 minutes, 45 minutes, 50 minutes, 55 minutes, 60 minutes, 65 minutes, 70 minutes, 75 minutes, and 80 minutes. In various, the time *Bordetella avium* isolates are exposed to the mutagenic agent is between any two times from above.

In various embodiments, the temperature sensitive *Bordetella avium* multivalent vaccine is a bivalent vaccine and the method of preparing the bivalent vaccine further includes isolating two *Bordetella avium* isolates from turkey poults. In various embodiments, the temperature sensitive *Bordetella avium* multivalent vaccine is a trivalent vaccine and the method of preparing the trivalent vaccine further includes isolating three *Bordetella avium* isolates from turkey poults. In other embodiments, the temperature sensitive *Bordetella avium* multivalent vaccine is a quadrivalent vaccine and the method of preparing the quadrivalent vaccine further includes isolating four *Bordetella avium* isolates from turkey poults.

In various embodiments, the method of preparing the multivalent vaccine includes the plurality of *Bordetella avium* isolates at least one or each being isolated from turkey poults that died from *Bordetella avium* rhinotracheitis or coryza. In various embodiments, the plurality of *Bordetella avium* are isolated from tracheas of the deceased poults, where each of the plurality of *Bordetella avium* isolates belong to *Bordetella avium* strains preferably having a mortality rate that is greater than 15% in turkeys. The plurality of *Bordetella avium* isolates of various embodiments are isolated from lower tracheas or lungs of the deceased poults In various embodiments, the method of preparing the multivalent vaccine includes exposing at least one of temperature sensitive strains of *Bordetella avium* to the mutagenic agent, where the at least one of temperature sensitive *Bordetella avium* strains stably grows at 32° C. at a rate and at 40° C. at rate slower than the rate at 32° C.

In various embodiments, the method of preparing the multivalent vaccine includes exposing at least one of temperature sensitive strains of *Bordetella avium* to the mutagenic agent, where the at least one of temperature sensitive *Bordetella avium* strains stably grows at 32° C. and not at 40° C.

In various embodiments, the method of preparing the multivalent vaccines further includes testing the growth of the temperature sensitive *Bordetella avium* strains where each of the temperature sensitive *Bordetella avium* strains preferably have different log phase growth curves at 32° C. over a time period.

In various embodiments are disclosed methods of immunizing turkey poults against *Bordetella avium*, comprising a step of administering to a turkey poult an immunologically effective amount of a temperature sensitive *Bordetella avium* multivalent vaccine comprising a pharmaceutically acceptable carrier and a plurality of different temperature sensitive *Bordetella avium* strains that are stably unable to colonize lower tracheas and lungs of the turkey poults.

In various embodiments, the temperature sensitive *Bordetella avium* multivalent vaccine is a bivalent vaccine with two different temperature sensitive *Bordetella avium* strains. In various embodiments, the temperature sensitive *Bordetella avium* multivalent vaccine is a trivalent vaccine with three different temperature sensitive *Bordetella avium* strains. In other embodiments, the temperature sensitive *Bordetella avium* multivalent vaccine is a quadrivalent vaccine with four different temperature sensitive *Bordetella avium* strains.

In various embodiments, the multivalent vaccine is administered nasally where the dosage of the plurality of different temperature sensitive *Bordetella avium* strains in the vaccine is about 50 to 200 million bacteria. In various embodiments, the multivalent vaccine is administered via addition to drinking water at a concentration of $10^5$, $10^6$, and $10^7$ bacteria per milliliter of water. In various embodiments, the multivalent vaccine is administered in one round to turkey poults at 2 to 3 weeks of age and, optionally, with an additional administration when the turkey poults are 4 to 6 weeks.

In various embodiments are disclosed a temperature sensitive *Bordetella avium* multivalent vaccine prepared by a process comprising the steps of: isolating a plurality of *Bordetella avium* isolates from turkey poults, where each of the *Bordetella avium* isolates is acquired at a different geographic location; separately exposing each of the plurality of *Bordetella avium* isolates to a mutagenic agent; separately culturing each of the plurality of *Bordetella avium* isolates after exposure with the mutagenic agent; isolating a temperature sensitive *Bordetella avium* strain from each culture of the plurality of *Bordetella avium* isolates, wherein each of the temperature sensitive strains at 32° C. stably grows at a rate and at 40° C. grows at a rate slower than the rate at 32° C.; and combining immunologically effective amounts of each of the temperature sensitive *Bordetella avium* strains with a pharmaceutically acceptable carrier.

The following are examples of various embodiments of the present invention.

EXAMPLE

*Bordetella avium* was isolated and identified at the Utah State University Central Utah Veterinary Diagnostic Laboratory from tracheal swabs taken from three farms in the Sanpete Valley of Utah and designated as BB, OC, and CS (i.e. BB-1, CS-9, OC-2). Five *Bordetella avium* isolates were isolated from turkeys showing clinical signs of respiratory disease and increased mortality in Sanpete County Utah, despite receiving the *Bordetella avium* vaccine. To determine if recent *Bordetella avium* isolates are related, or unrelated to the vaccine strain (e.g. vaccine strain 87, ART VAX®, and/or ATCC No. 31770 as indicated in U.S. Pat. No. 4,379,140), the *Bordetella avium* isolates and the vaccine strain were collected for comparison by matrix-assisted laser desorption/ionization time of flight (MALDI-TOF) mass spectroscopy. Compared with other methods, including 16S rRNA and rpoB gene sequencing, reported accuracy of identification of bacteria, fungi or parasites has been 95.4% to 99.5%.

Spectra were obtained from clinical isolates collected from turkeys, grown overnight on blood agar plates, and evaluated by MALDI-TOF mass spectroscopy. The MALDI-TOF spectra from the five isolates were evaluated to determine relationships among the clinical isolates. This was done by comparing the MALDI-TOF results to the database of microorganisms using software for peak matching and by multivariate analyses using the three principal component scores. 3D scatter plots and Process for Principal Component Analysis dendograms were then used to visualize how closely correlated the bacteria are based on the first three principal component scores of their protein signatures. Four of five isolates were in the same cluster as the vaccine strain and one isolate did not cluster with the vaccine strain. For future studies, Hemagglutination (HA) assays will be done to identify species as *Bordetella avium* agglutinates red blood cells and other species of *Bordetella* do not; Hemagglutination inhibition (HAI) assays will be done to find serological differences between the vaccine and other isolates to answer whether the serum from a vaccinated turkey will protect against other isolates; and Polymerase chain reaction (PCR) assays will be used to confirm the species that were tested as well as 6S rRNA and rpoB gene sequencing.

The one *Bordetella avium* isolate (which was designated CS) that did not cluster with the vaccine strain had a significantly higher mortality rate than the other isolates.

Two of the other four *Bordetella avium* isolates that did cluster with the vaccine straine were selected and designated BB and OC.

The isolates were transported to Brigham Young University. Small, non lactose fermenting colonies were passaged onto Brain Heart Infusion (BHI) agar to isolate *Bordetella* like colonies. All cultures were incubated at 32° C. unless otherwise stated.

Temperature sensitive mutants were generated as previously described using chemical mutagenesis. Saturated cultures were incubated with 1 mg/mL N-methyl-N-nitro-N-nitrosoguanidine (NTG) for 1 hour. Mutated cultures were washed and the culture was spread onto tryptic soy agar (TSA). Plates were incubated at 32° C. for 48 hours. These plates were then replicated and incubated at both 32° C. and 40° C. for 48 hours. Colonies which grew at 32° C. and not 40° C. were selected and passaged onto TSA plates and incubated at 32° C. and 40° C. to confirm temperature sensitivity.

FIG. 1 shows the growth curves for mutants selected for the trivalent vaccine. As shown in FIG. 1, growth curves were then performed on colonies that showed inhibited growth at 40° C. Mutants were then inoculated intranasally into two-week-old poults. After two weeks, nasal mucosa and tracheal swabs were taken and incubated on MAC plates for 48 hours to determine the level of colonization by small non-lactose fermenting organisms. Serum antibodies were tested at four weeks post inoculation.

FIG. 2 shows colonization of mutants selected for the trivalent vaccine. 14 days post inoculation, nasal and tracheal passages were swabbed for colonization. Colonization was rated on a scale from 1-5 with 5 indicating heavy growth of small non-lactose fermenting organisms.

As shown in FIG. 2, mutants that exhibited poor or no growth at 40° C., colonized the nasal mucosa, but not the trachea, and induced serum antibodies were selected for candidates for the trivalent vaccine. Single mutants (BB-1, CS-1 and OC-1) of each strain that exhibited poor growth at 40° C. were selected for preliminary trials in a trivalent vaccine. Poults were inoculated though drinking water and observed for symptoms of disease. This preliminary vaccine showed marked success in preventing disease in poults, although it seemed to produce some slight symptoms in the birds. Tests in isolated poults for vaccine colonization of these strains showed that BB-1 was likely the cause of the mild symptoms, while the CS-1 mutant was fatal to the birds. As a result double mutants of these isolates were produced using the same NTG procedure and retested in isolated birds for nasal mucosa colonization. CS-1 Double Mutant (DM) 9 showed poor growth at 40° C. and excellent colonization in the nasal mucosa.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

The following references are incorporated by reference:

[1] Burke, D. S. and M. Jensen (1980). "Immunization against turkey coryza by colonization with mutants of *Alcaligenes faecalis*." Avian Diseases: 726-733.

[2] Burke, D. S. and M. M. Jensen (1981). "Field Vaccination Trials Against Turkey Coryza Using a Temperature-Sensitive Mutant of *Alcaligenes faecalis*." Avian Diseases 25(1): 96-103.

[3] Jensen, M. M. and M. S. Marshall (1981). "Control of a Turkey *Alcaligenes* Rhinotracheitis in Utah with a Live Vaccine." Avian Diseases 25(4): 1053-1057.

What is claimed is:

1. A method of preparing a temperature sensitive *Bordetella avium* multivalent vaccine, the method comprising the steps of:
    a) isolating a plurality of *Bordetella avium* isolates from turkey poults, where each of the plurality of *Bordetella avium* isolates are acquired at different geographic locations;
    b) individually exposing each of the plurality of *Bordetella avium* isolates to a mutagenic agent;
    c) individually culturing each of the plurality of *Bordetella avium* isolates after exposure to the mutagenic agent;
    d) isolating a temperature sensitive *Bordetella avium* strain from each culture of the plurality of *Bordetella avium* isolates, wherein each of the temperature sensitive *Bordetella avium* strains at 32° C. stably grows at a rate and at 40° C. grows at a rate slower than the rate at 32° C.; and
    e) combining immunologically effective amounts of each of the temperature sensitive *Bordetella avium* strains with a pharmaceutically acceptable carrier.

2. The method of claim 1, where the temperature sensitive *Bordetella avium* multivalent vaccine is a bivalent vaccine and the plurality of *Bordetella avium* isolates of step a) consists essentially of two *Bordetella avium* isolates from turkey poults.

3. The method of claim 1, where the temperature sensitive *Bordetella avium* multivalent vaccine is a trivalent vaccine and the plurality of *Bordetella avium* isolates of step a) consists essentially of three *Bordetella avium* isolates from turkey poults.

4. The method of claim 1, where the plurality of *Bordetella avium* isolates are each isolated from turkey poults that died from *Bordetella avium* rhinotracheitis.

5. The method of claim 1, wherein each of the plurality of the plurality of *Bordetella avium* isolates are isolated from tracheas of the poults.

6. The method of claim 1, where each of the plurality of *Bordetella avium* isolates belong to *Bordetella avium* strains having a mortality rate that is greater than 15% in turkeys.

7. The method of claim 1 further comprising the step of exposing at least one of temperature sensitive strains of *Bordetella avium* of step d) to a second mutagenic agent, where the at least one of temperature sensitive *Bordetella avium* strains stably grows at 32° C. and not at 40° C.

8. The method of claim 1, wherein the temperature sensitive *Bordetella avium* strains of step d) have different log phase growth curves at 32° C.

9. The method of claim 1 further comprising the steps of acquiring matrix-assisted laser desorption/ionization time of flight spectras of each of the plurality of *Bordetella avium* isolates of step a) and comparing the spectras to a matrix-assisted laser desorption/ionization time of flight spectra of vaccine 87 of *Bordetella avium*, ATCC No. 31770, wherein *Bordetella avium* isolates identified as having spectras different from vaccine strain 87 of *Bordetella avium*, ATCC No. 31770 are individually exposed to the mutagenic agent of step b).

10. A temperature sensitive *Bordetella avium* multivalent vaccine comprising a pharmaceutically acceptable carrier and a plurality of temperature sensitive *Bordetella avium* strains, wherein at least one of the plurality of temperature sensitive *Bordetella avium* strains is prepared from a *Bor-*

*detella avium* isolate having a matrix-assisted laser desorption/ionization time of flight spectra that differs from a matrix-assisted laser desorption/ionization time of flight spectra of vaccine strain 87 of *Bordetella avium*, ATCC No, 31770.

11. The temperature sensitive *Bordetella avium* multivalent vaccine of claim 10 prepared by a process comprising the steps of:
   a) isolating a plurality of *Bordetella avium* isolates from turkey poults, where each of the *Bordetella avium* isolates is acquired at a different geographic location;
   b) separately exposing each of the plurality of *Bordetella avium* isolates to a mutagenic agent;
   c) separately culturing each of the plurality of *Bordetella avium* isolates after exposure with the mutagenic agent;
   d) isolating one of the plurality of temperature sensitive *Bordetella avium* strains from each culture of the plurality of *Bordetella avium* isolates, wherein each of the plurality of temperature sensitive *Bordetella avium* strains at 32° C. stably grows at a rate and at 40° C. grows at a rate slower than the rate at 32° C.; and
   e) combining immunologically effective amounts of each of the plurality of temperature sensitive *Bordetella avium* strains with a pharmaceutically acceptable carrier.

12. A temperature sensitive *Bordetella avium* multivalent vaccine comprising a pharmaceutically acceptable carrier and a plurality of temperature sensitive *Bordetella avium* strains, wherein each of the plurality of temperature sensitive *Bordetella avium* strains are stably unable to colonize lower tracheas and lungs of turkey poults.

13. The temperature sensitive *Bordetella avium* multivalent vaccine of claim 12, where each of the plurality of temperature sensitive *Bordetella avium* strains has a different colonization rate in a nasal mucosa or upper trachea mucosa after administration.

14. The temperature sensitive *Bordetella avium* multivalent vaccine of claim 12, wherein the plurality of temperature sensitive *Bordetella avium* strains consists essentially of two temperature sensitive *Bordetella avium* strains.

15. The temperature sensitive *Bordetella avium* multivalent vaccine of claim 12, wherein the plurality of temperature sensitive *Bordetella avium* strains consists essentially of three temperature sensitive *Bordetella avium* strains.

16. The temperature sensitive *Bordetella avium* multivalent vaccine of claim 12, wherein each of the plurality of temperature sensitive *Bordetella avium* strains stably grows at a rate at 32° C. and at 40° C. grows at a rate slower than the rate at 32° C.

17. The temperature sensitive *Bordetella avium* multivalent vaccine of claim 12 prepared by a process comprising the steps of:
   a) isolating a plurality of *Bordetella avium* isolates from turkey poults, where each of the *Bordetella avium* isolates is acquired at a different geographic location;
   b) separately exposing each of the plurality of *Bordetella avium* isolates to a mutagenic agent;
   c) separately culturing each of the plurality of *Bordetella avium* isolates after exposure to the mutagenic agent;
   d) isolating one of the plurality of temperature sensitive *Bordetella avium* strains from each culture of the plurality of *Bordetella avium* isolates, wherein each of the plurality of temperature sensitive *Bordetella avium* strains at 32° C. stably grows at a rate and at 40° C. grows at a rate slower than the rate at 32° C.; and
   e) combining immunologically effective amounts of each of the plurality of temperature sensitive *Bordetella avium* strains with a pharmaceutically acceptable carrier.

\* \* \* \* \*

UNITED STATES PATENT AND TRADEMARK OFFICE
CERTIFICATE OF CORRECTION

PATENT NO. : 10,071,149 B2
APPLICATION NO. : 15/586110
DATED : September 11, 2018
INVENTOR(S) : Marcus M. Jensen et al.

It is certified that error appears in the above-identified patent and that said Letters Patent is hereby corrected as shown below:

In the Claims

Column 10, Line 29, Claim 2:
After "essentially of two"
Delete "*Bordetella avium*isolates" and
Insert -- *Bordetella avium* isolates --.

Column 10, Line 34, Claim 3:
After "essentially of three"
Delete "*Bordetella avium*isolates" and
Insert -- *Bordetella avium* isolates --.

Column 10, Lines 36-37, Claim 4:
After "the plurality of"
Delete "*Bordetella avium*isolates" and
Insert -- *Bordetella avium* isolates --.

Column 10, Line 39, Claim 5:
After "wherein each of the plurality of"
Delete "the plurality of" (second occurrence).

Column 10, Lines 57-58, Claim 9:
After "flight spectra of vaccine"
Insert -- strain --.

Column 10, Line 63, Claim 10:
Delete "*Bordetella avium*multivalent" and
Insert -- *Bordetella avium* multivalent --.

Signed and Sealed this
Twelfth Day of March, 2019

Andrei Iancu
*Director of the United States Patent and Trademark Office*

CERTIFICATE OF CORRECTION (continued)
U.S. Pat. No. 10,071,149 B2

Column 11, Line 6, Claim 11:
Delete "*Bordetella avium*multivalent" and
Insert -- *Bordetella avium* multivalent --.

Column 11, Line 17, Claim 11:
Delete "*Bordetella avium*strains" and
Insert -- *Bordetella avium* strains --.

Column 11, Line 25, Claim 12:
Delete "*Bordetella avium*multivalent" and
Insert -- *Bordetella avium* multivalent --.

Column 11, Lines 31-32, Claim 13:
Delete "*Bordetella avium*multivalent" and
Insert -- *Bordetella avium* multivalent --.

Column 12, Lines 1-2, Claim 14:
Delete "*Bordetella avium*multivalent" and
Insert -- *Bordetella avium* multivalent --.

Column 12, Line 3, Claim 14:
Delete "*Bordetella avium*strains" and
Insert -- *Bordetella avium* strains --.

Column 12, Lines 5-6, Claim 15:
Delete "*Bordetella avium*multivalent" and
Insert -- *Bordetella avium* multivalent --.

Column 12, Line 7, Claim 15:
Delete "*Bordetella avium*strains" and
Insert -- *Bordetella avium* strains --.

Column 12, Lines 9-10, Claim 16:
Delete "*Bordetella avium*multivalent" and
Insert -- *Bordetella avium* multivalent --.

Column 12, Lines 14-15, Claim 17:
Delete "*Bordetella avium*multivalent" and
Insert -- *Bordetella avium* multivalent --.

Column 12, Line 25, Claim 17:
Delete "*Bordetella avium*strains" and
Insert -- *Bordetella avium* strains --.